United States Patent [19]
Goldberg et al.

[11] Patent Number: 5,498,636
[45] Date of Patent: Mar. 12, 1996

[54] TREATMENT OF ANGINA PECTORIS

[75] Inventors: Arthur H. Goldberg, Montclair, N.J.; Leonard Lachman, Fort Salonga, N.Y.

[73] Assignee: RiboGene, Inc., Hayward, Calif.

[21] Appl. No.: 349,149

[22] Filed: Dec. 2, 1994

Related U.S. Application Data

[63] Continuation of Ser. No. 53,440, Apr. 28, 1993, abandoned, which is a continuation of Ser. No. 850,494, Mar. 13, 1992, abandoned.

[51] Int. Cl.$^6$ ............ A61K 31/535; A61K 31/405; A61K 31/165; A61K 31/135
[52] U.S. Cl. ............ 514/652; 514/236.2; 514/415; 514/620
[58] Field of Search ............ 514/236.24, 415, 514/620, 652

[56] References Cited

U.S. PATENT DOCUMENTS 4,428,883  1/1984  Hussain ............ 424/248.51

*Primary Examiner*—Kimberly Jordan
*Attorney, Agent, or Firm*—Pennie & Edmonds

[57] ABSTRACT

This invention relates to a method for treating angina pectoris. Pursuant to this method, a β-adrenergic-blocking agent is administered acutely to a person having angina to provide an essentially immediate, therapeutic amount of bioavailable blocking agent. The invention further relates to a method wherein the blocking agent is nasally administered for this purpose.

18 Claims, 1 Drawing Sheet

TREATMENT OF ANGINA PECTORIS

This is a continuation of application Ser. No. 08/053,440, filed Apr. 28, 1993, now abandoned, which is a continuation of application Ser. No. 07/850,494, filed Mar. 13, 1992 and now abandoned.

BACKGROUND OF THE INVENTION

1. Field of Invention

The present invention relates to a novel method for treatment of angina pectoris. A β-adrenergic-blocking agent is administered acutely to a patient having angina. The dose is desirably provided by nasal administration to provide an essentially immediate, therapeutically effective amount of blocking agent to treat the angina.

2. Description of the Prior Art

Angina occurs when cardiac work and myocardial oxygen demand exceed the ability of the coronary arteries to supply oxygenated blood. The myocardium becomes ischemic and, accompanied by myriad physiological and chemical changes, symptoms such as pain result.

The discomfort of angina pectoris is most commonly felt beneath the sternum. It may range from a vague ache to an intense precordial crushing sensation. It may also radiate, usually to the left shoulder and arm, but also through the back, into the throat, jaws and/or teeth and elsewhere. Anginal discomfort may even be felt in the upper or lower abdomen.

Angina is characteristically triggered by physical exercise. The response to exercise is usually predictable but, in some patients, a given stress may be tolerated one day and precipitate angina the next. Attacks vary in frequency, being separated by symptom-free intervals of as long as weeks, months, and even years. They may also increase to a fatal outcome.

β-adrenergic-blocking agents are well known for the prophylaxis of angina. However, these blocking agents have not generally been shown to be effective for acute uses such as the management of an angina attack. Once an attack has commenced, the treatment of choice is normally nitroglycerin.

As a result of the foregoing, a normal procedure for individuals subject to angina involves the daily administration of a prophylactic dosage of a β-adrenergic-blocking agent such as propranolol. This essentially involves maintaining a therapeutic level or concentration of blocking agent in a person's bloodstream on a long term basis which may be indefinite in duration.

That procedure has been shown to be effective in reducing the frequency of angina attacks in humans. A drawback, however, is the requirement for virtually constant drug therapy. Various adverse reactions to β-adrenergic-blocking agents are known. In particular, at the high level of dosage utilized for prophylaxis, there are possibilities of side effects such as bradycardia, hypotension and dizziness. Further, abrupt discontinuance of the drug has still other potential effects including the precipitation or exacerbation of angina, myocardial infarction and ventricular dysrhythmias.

Another drawback of that procedure involves individuals having certain complications. For example, those who are pregnant, suffering hepatic impairment or having bronchitis or emphysema can be subjected to its long term, virtually constant drug exposure only under closely monitored conditions, if at all. Consequently, many prospective patients are precluded from the benefits of that procedure.

SUMMARY OF THE INVENTION

In view of the foregoing, it is apparent that a serious need exists for an improved method of utilizing β-adrenergic-blocking agents for the control of angina pectoris. Thus, it is an object of the present invention to devise a method whereby these blocking agents may also be utilized acutely to treat angina.

It has been discovered that the foregoing objectives may be achieved by the selective administration of β-adrenergic-blocking agents to provide an essentially immediate, therapeutically effective amount of blocking agent to a person having angina. In this manner, these agents can treat the attack itself, correcting the signs and reducing the symptoms of angina.

It has been discovered that the β-adrenergic-blocking agent is desirably provided in a composition suitable for nasal administration. This ensures prompt and efficient delivery of the blocking agent to the sites governing angina. In accordance with the method of the present invention, these blocking agents successfully treat and may even abort an attack of angina.

DETAILED DESCRIPTION OF THE INVENTION

Figure 1:
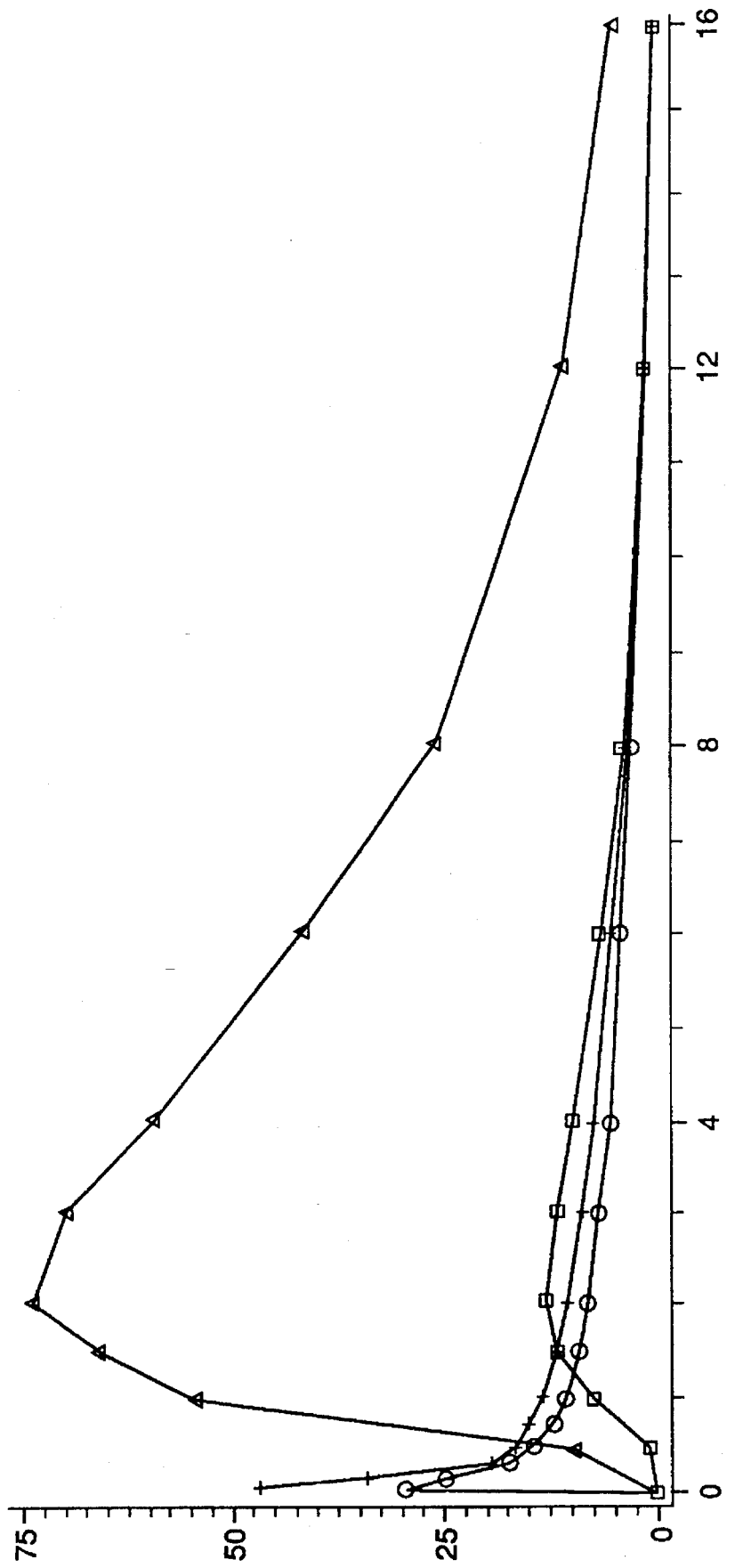
FIG. 1 is a graph of plasma concentration, measured as a function of time, of β-adrenergic-blocking agent administered pursuant to different means.

Attacks of angina pectoris are ordinarily quite brief. They usually persist no longer than a few minutes. While attacks can lead directly to permanent heart damage and/or death, they more commonly subside due to the inactivity forced on can individual by the attendant pain. At rest, the body's myocardial oxygen demand usually drops to a level which the coronary artery system an supply. This permits an individual to recover naturally from most attacks. Because of the potentially serious repercussions of an attack, however, some form of drug therapy is often employed to assist the body in recovering from an attack.

According to the present invention, it has been discovered that a β-adrenergic-blocking agent can be effective for the acute treatment of angina. If the blocking agent is introduced in a therapeutically effective amount promptly after the attack commences, it can treat the angina, reducing its associated symptoms. These blocking agents may be administered only as needed and in reduced dosage amount as compared to a prophylactic procedure.

In contrast to the prior art procedure involving frequent, purely prophylactic dosages of blocking agent, the present invention involves a targeted administration. The drug is administered acutely when there is an indication for an angina attack. This permits a direct and less intrusive use of β-adrenergic-blocking agents. They may be administered only as needed and in reduced dosage amount as compared to a prophylactic procedure. As a consequence, occurrences of adverse drug reaction, overdosage and/or discontinuance reaction are markedly reduced. This extends the availability of blocking agents to many classes of patients suffering from angina.

In accordance with the present invention, the dosage requirements for β-adrenergic-blocking agent are greatly reduced. In the prior art, it was customary to provide sufficient blocking agents to maintain an effective concentration in the blood stream over an extended time. Doses would be repeated chronically, daily for life. For the present invention, administration is specific to an actual attack and the drug is intended to function immediately, only while it lasts. Consequently, far less blocking agent is required.

For example, pursuant to the prior art procedure of prophylactic doses of β-adrenergic-blocking agent, it is customary to administer no less than about 80 mg, and up to to about 320 mg, of propranolol hydrochloride per day. For the targeted method of the present invention, however, the analogous dose is normally from 2.5 to 30 mg, preferably from 5 to 10 mg, of β-adrenergic-blocking agent. In addition, it is administered only when its need is apparent. This reduction exposes a patient to far less risk of an adverse drug reaction.

Even where such a prophylactic method is employed by an individual to control angina, attacks may occur. These so-called "breakthrough" attacks are usually attributed to unusual physical or even emotional stress. They have heretofore been treated in the same manner as any other attack, for example, with nitroglycerin.

These breakthrough attacks may also be treated in accordance with the method of this invention. Accordingly, it is not necessary for an individual on prophylaxis with a β-adrenergic-blocking agent to change medication in the event of an attack. Additional blocking agent may be administered to obtain a therapeutically effective amount. Thus, it is possible to control angina both prophylactically and in the event of an attack with a β-adrenergic-blocking agent. Acute usage for breakthrough is not, however, limited to instances where a blocking agent was utilized for prophylaxis. β-adrenergic-blocking agent may be utilized in conjunction with other chronically administered, prophylactic drugs.

In the acute treatment of angina, it is important to insure the prompt entry of the β-adrenergic-blocking agent into the bloodstream. For this reason, the blocking agent may be provided in injectable form and administered parenterally. Another means of achieving essentially immediate, effective bioavailability is by systemic administration of the blocking agent. A preferred systemic technique of nasal administration is described in, for example, U.S. Pat. Nos. 4,394,390 and 4,428,883 of Anwar A. Hussain et al, the disclosures of which are incorporated herein by reference.

In accordance with the foregoing, preferred dosage forms of the present invention comprise a β-adrenergic-blocking agent in a pharmaceutically acceptable nasal carrier. Any of the blocking agents can be conveniently administered in such a carrier. These compositions comprise a systemic, therapeutically effective amount of the desired drug together with a pharmaceutically acceptable nasal carrier.

Nasal carriers suitable in accordance with the present invention will be apparent to those skilled in the art of nasal pharmaceutical formulations. Exemplary nasal carriers include saline solutions; glycols such as propylene glycol; glycol ethers such as polyethylene glycol and combinations of the foregoing with water and/or one another. For still other examples, reference is made to the text entitled "REMINGTON'S PHARMACEUTICAL SCIENCES", 14th edition, 1970.

The choice of a suitable carrier in accordance with the present invention will depend on the exact nature of the particular nasal dosage form required. A therapeutic agent may, for example, be formulated into a nasal solution (for use as drops or as a spray), a nasal suspension, a nasal ointment, a nasal gel or any other nasal form. Preferred nasal dosage forms are solutions, suspensions or gels. These normally contain a major amount of water (preferably purified water) in addition to the active ingredient. Desirably, these compositions comprise at least 60% water by total weight.

Minor amounts of other ingredients such as tonicity agents (e.g. NaCl), pH adjusters (e.g., a base such as NaOH), emulsifiers or dispersing agents, buffering agents, preservatives, wetting agents, thickening agents (e.g. polyvinyl alcohol) and gelling agents (e.g. polaxamer) may also be present. Particularly preferred compositions contain sufficient amounts of the foregoing and/or other ingredients to be a substantially isotonic and/or buffered to a physiologically acceptable pH.

As previously discussed, the efficacy of a β-adrenergic-blocking agent is dependent upon its essentially immediate presence at the site of desired drug activity. This is commonly reflected by its concentration in the blood of the subject being treated. It is therefore particularly significant that the present nasal administration of β-adrenergic-blocking agent is characterized by a virtually instantaneous and pronounced blood concentration as compared to oral procedure of administration.

Those skilled in the art will be aware that a therapeutically effective amount of a particular β-adrenergic-blocking agent will vary with the particular drug as well as the type, age, size, weight and general physical condition of the subject. The amount will also vary dependent upon the particular therapeutic effect desired. Typically, however, the dosage level will be significantly less than the dosage levels currently employed for analogous prophylaxis treatment.

Any of the β-adrenergic-blocking agents known in the art may be utilized in accordance with the present invention. This includes blocking agents in their basic states or as their acid addition salts. Certain β-adrenergic-blocking agents are, however, preferred. These include propranolol, nadolol, timolol, metoprolol, atenolol, labetolol, pindolol, oxprenolol and their salts. Of these, timolol and especially propranolol (or their salts) are particularly preferred.

In formulation of the present compositions, a relatively water soluble form of β-adrenergic-blocking agent is usually employed. Use of a fully dissolved or solubilized blocking agent maximizes its immediate effect. This insures an essentially immediate, elevated effect.

The following is given by way of illustration only and is not to be considered limitative of this invention. Many apparent variations are possible without departing from the spirit and scope thereof.

EXAMPLE

A panel of individuals who were subject to attacks of angina pectoris were randomly divided into two groups to perform a double blind, cross-over study. The study was predicated on a customary United States Federal Food and Drug exercise tolerance protocol involving a standard treadmill procedure.

For the study, each person first exercised under the influence of either a 0.1 ml placebo or active spray, the latter containing 5 mg of propranolol hydrochloride. The person's condition was constantly monitored and exercise discontinued as soon as each person experienced angina symptoms or a 1 mm depression of the ST segment on his electrocardiogram. One week later, the individuals repeated this stress tolerance test with the alternate spray. This permitted direct patient comparisons and a normalized group statistical analysis for differences in result due to the presence of β-adrenergic-blocking agent.

During the tests, each person was evaluated respecting angina onset time, peak exercise time, maximum blood pressure and heart rate. Data from all the individuals was then correlated into scores for each of these categories incurred utilizing placebo or active spray. The results from these calculations are set forth in the Table below.

| SPRAY | ANGINA ONSET (Sec.) | PEAK EXERCISE (Sec.) | MAXIMUM BLOOD PRESSURE (mm of Hg) | RESTING BLOOD PRESSURE (mm of Hg) | MAXIMUM HEART RATE (/min) | MINIMUM HEART RATE (/min) |
|---|---|---|---|---|---|---|
| PLACEBO | 330 | 460 | 195/97 | 152/90 | 132 | 79 |
| ACTIVE | 369 | 529 | 185/90 | 155/92 | 120 | 73 |
| CHANGE | 12% | 15% | 5%/8% | −2%/−2% | 10% | 8% |

This data shows a significant increase in the ability of a person to withstand physical stress when under the influence of a therapeutically effective amount of bioavailable β-adrenergic-blocking agent. In correlation with this increased exercise tolerance, there is a decrease in the patient's vital signs. Moreover, this reduction is more marked under stressed conditions.

These results clearly reflect that propranolol, in addition to its prophylactic use for control of angina, can successfully treat an attack of angina.

In further investigation of these surprising results, propranolol was administered to individuals on isolated days by three different routes. It was taken orally, through injection and nasally by spray. Each person's blood was assayed before and after each administration for propranolol concentration. The results of this investigation were then graphed in FIG. 1.

On this graph, the Y-axis reflects plasma propranolol concentration in nanograms per milliliter (ng/ml); the X-axis, time in hours after dosage. Plot points for the different routes of administration are designated respectively as: oral, squares and triangles; injection, plus signs; and nasal, circles. The oral dosages were performed by way of a tablet containing either 20 or 80 mg, respectively, while the injection and nasal dosages were each 5 mg of propranolol As shown by FIG. 1, a maximum blood level concentration of propranolol is reached almost immediately by either injection or nasal administration. In both instances, these concentrations reach about 47 ng/ml (injection) and 32 ng/ml (nasal) within five minutes. After oral administration, on the other hand, the plasma concentration of propranolol increases much more slowly. Even at a dosage rate of 80 mg, sixteen times that employed for injection or nasal administration, as much as an hour is required before a comparable concentration is obtained through an oral dosage. At an oral dosage rate of 20 mg, the peak concentration is reached in two hours and remains only a fraction of that achieved essentially immediately by the injection or nasal routes for their much smaller doses. Thus, only through much faster means than oral administration can a person achieve a therapeutically effective amount of drug within the span of time necessary for treatment of angina.

This investigation suggests that past failures to appreciate that β-adrenergic-blocking agent could be effective for more than prophylaxis of angina may have resulted from a combination of factors. Firstly, the prior art does not appear to recognize the effectiveness of acute administration of a β-adrenergic-blocking agent to control angina. Secondly, its reliance on conventional, oral routes of administration would have practically precluded essentially immediately achieving an effective amount of this drug (as reflected, for example, by its concentration in the blood) within the short span of time necessary for treatment.

While this invention has been described and illustrated with reference to certain preferred embodiments thereof, those skilled in the art will appreciate that various changes, modifications and substitutions can be made therein without departing from the spirit of the invention. Such expected differences in the practice of the present invention and the results obtained are contemplated in accordance with the objects and practices of the present invention. It is intended, therefore, that the invention be limited only by the scope of the claims which follow.

What is claimed is:

1. A method for the acute treatment of a person having angina pectoris comprising nasally or intravenously administering a β-adrenergic-blocking agent systemically to provide an essentially immediate, therapeutically effective amount of blocking agent to a person while said person is experiencing an attack of angina pectoris in a single dose range of about 2.5 to 30 mg.

2. The method of claim 1, wherein the blocking agent comprises propranolol or a salt thereof.

3. The method of claim 1, wherein the blocking agent is administered in a nontoxic pharmaceutically acceptable nasal carrier.

4. The method of claim 3, wherein the β-adrenergic-blocking agent is selected from the group consisting of propranolol, nadolol, timolol, metoprolol, atenolol, labetolol, pindolol, oxprenolol and a salt thereof.

5. The method of claim 3, wherein from 5 to 10 mg of propranolol hydrochloride is administered.

6. The method of claim 1, wherein the composition is selected from the group consisting of a solution or suspension.

7. The method of claim 6, wherein the carrier comprises at least 60 percent water by total weight.

8. The method of claim 7, wherein the composition is isotonic and buffered to the pH of blood serum.

9. The method of claim 8, wherein the blocking agent in the composition is completely solubilized.

10. The method of claim 9, wherein the β-adrenergic-blocking agent is selected from the group consisting of propranolol, nadolol, timolol, metoprolol, atenolol, labetolol, pindolol, oxprenolol and a salt thereof.

11. The method of claim 9, wherein the blocking agent comprises propranolol hydrochloride.

12. The method of claim 11, wherein from 5 to 10 mg of blocking agent is administered.

13. A method for the acute treatment of a person having angina pectoris comprising nasally or intravenously administering a β-adrenergic-blocking agent systemically to provide an essentially immediate, therapeutically effective amount of blocking agent to a person during a breakthrough attack while said person is subject to prophylaxis with chronic doses of prophylactic amounts of β-adrenergic-blocking agent.

14. The method of claim 13, in which from 2.5 to 30 mg of β-adrenergic-blocking agent is nasally administered.

15. The method of claim 13, wherein the blocking agent is systemically administered in an aqueous solution or suspension.

16. The method of claim 15, wherein the blocking agent is selected from the group consisting of propranolol, nadolol, timolol, metoprolol, atenolol, labetolol, pindolol, oxprenolol and a salt thereof.

17. The method of claim 16, wherein from 2.5 to 30 mg of blocking agent in completely solubilized form is administered.

18. The method of claim 13, wherein from 5 to 10 mg of propranolol hydrochloride is administered.

* * * * *